(12) United States Patent
De Martino et al.

(10) Patent No.: US 8,214,024 B2
(45) Date of Patent: Jul. 3, 2012

(54) ELECTRONIC POLARIMETRIC IMAGING SYSTEM FOR A COLPOSCOPY DEVICE AND AN ADAPTER HOUSING

(75) Inventors: Antonello De Martino, Massy (FR); Bernard Drevillon, Clamart (FR); Laurent Schwartz, Paris (FR); André Nazac, Paris (FR); Bernard Huynh, Paris (FR)

(73) Assignees: Ecole Polytechnique, Palaiseau (FR); Assistance Publique-Hopitaux de Paris, Paris (FR); Institut Mutualiste Montsouris, Paris (FR); Bernard Huynh, Malakoff (FR)

( * ) Notice: Subject to any disclaimer, the term of this patent is extended or adjusted under 35 U.S.C. 154(b) by 904 days.

(21) Appl. No.: 11/994,177

(22) PCT Filed: Jun. 27, 2006

(86) PCT No.: PCT/FR2006/050634
§ 371 (c)(1),
(2), (4) Date: Apr. 16, 2008

(87) PCT Pub. No.: WO2007/003840
PCT Pub. Date: Jan. 11, 2007

(65) Prior Publication Data
US 2008/0200817 A1     Aug. 21, 2008

(30) Foreign Application Priority Data
Jul. 1, 2005   (EP) .................................... 05300550

(51) Int. Cl.
*G01J 4/00*      (2006.01)

(52) U.S. Cl. .......................... 600/476; 356/364; 356/369
(58) Field of Classification Search .................. 600/476, 600/178; 356/369, 364; 396/544; 1/1
See application file for complete search history.

(56) References Cited

U.S. PATENT DOCUMENTS 4,063,266 A * 12/1977 Thomas et al. ............... 396/544
4,523,848 A *  6/1985 Gorman et al. .............. 356/368

(Continued)

FOREIGN PATENT DOCUMENTS
EP         1 411 333 A1    4/2004

OTHER PUBLICATIONS

International Search Report of PCT/FR2006/050634 filed Jun. 27, 2006, date of mailing Apr. 18, 2007.

*Primary Examiner* — Long V. Le
*Assistant Examiner* — Farshad Negarestan
(74) *Attorney, Agent, or Firm* — Young & Thompson

(57) ABSTRACT

An electronic polarimetric imaging system for a colposcopy device designed for in vivo observation of a cervix, wherein the colposcopy device includes a light source for illuminating the observable cervix and at least visual elements for monitoring an image of the cervix, the illumination optical path towards the cervix and the image optical path coming back from the cervix being separated from one another over at least one portion of the paths thereof. The system includes a polarimetric adapter housing which is removable into the separated portion of the illumination and image optical paths, the polarimetric adapter housing including a polarisation state generator (PSG) on the illumination optical path and a polarisation analyser (PSA) on the image optical path, wherein the polarisation state generator (PSG) and the polarisation analyser (PSA) are controllable. Several levels of polarimetric characterisation are possible. An adaptor housing is also disclosed.

20 Claims, 6 Drawing Sheets

U.S. PATENT DOCUMENTS

Figure 1:
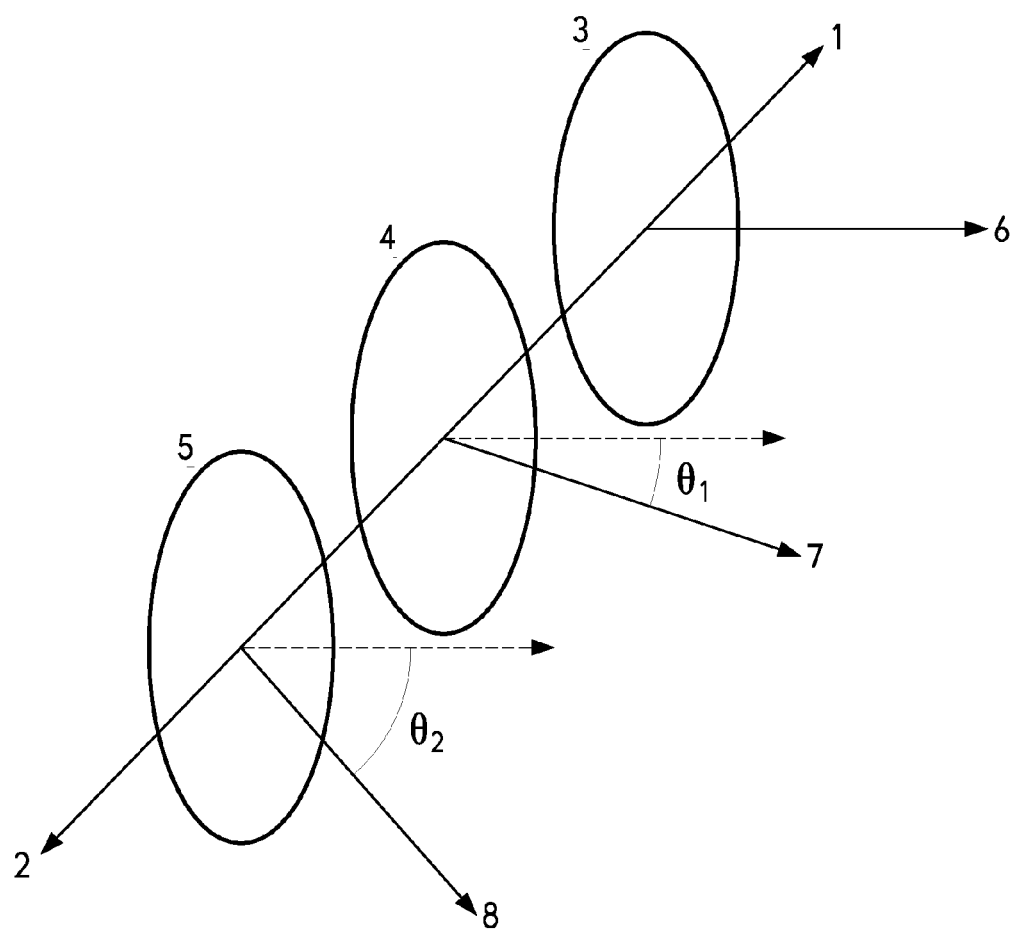

| | | | |
|---|---|---|---|
| 5,015,100 A * | 5/1991 | Doyle | 356/445 |
| 5,521,705 A * | 5/1996 | Oldenbourg et al. | 356/368 |
| 6,068,593 A * | 5/2000 | Krauter et al. | 600/178 |
| 6,175,412 B1 | 1/2001 | Drevillon et al. | |
| 6,393,431 B1 * | 5/2002 | Salvati et al. | 1/1 |
| 7,289,211 B1 * | 10/2007 | Walsh et al. | 356/369 |
| 2002/0007122 A1 | 1/2002 | Kaufman et al. | |
| 2004/0129867 A1 * | 7/2004 | Mackey | 250/225 |
| 2005/0090751 A1 | 4/2005 | Balas | |

* cited by examiner

ELECTRONIC POLARIMETRIC IMAGING SYSTEM FOR A COLPOSCOPY DEVICE AND AN ADAPTER HOUSING

The present invention relates to an electronic polarimetric imaging system for a colposcopy device as well as an adaptor housing designed for said apparatus to provide such a system. It finds application in the field of medical diagnosis of pathologies of the cervix.

Although it is one of the best controlled cancerous pathologies, cervical cancer stills induces relatively high mortality. Still this cancer is generally preceded by cellular abnormalities of the cervix called dysplasias which may be detected during routine examinations. The current practice is as follows: in case of suspicious smear, there is an in-depth examination with a colposcopy device (a binocular magnifying glass suited to this examination) during which the physician applies on the cervix 3% acetic acid, then Lugol (iodine dye): the abnormal zone become white in reaction with acetic acid and do not change colors when in contact with Lugol. This technique is very sensitive (very little false negative results) but very little specific (many false positive results): any abnormality, regardless whether it is benign or indicates a severe dysplasia, gives more or less the same response. Before making a decision, the gynaecologist may take biopsies, but the selection of the locations to be biopsied remains difficult, even for an experienced physician.

In practice, taking into account the vital risk for the patient, in case of doubt the gynaecologist makes the decision of performing a conisation, i.e. the ablation of a cone of a typical size of 2 cm in the front section of the cervix. The operating part is then subjected to histologic examination to obtain the final diagnosis. It appears thus a posteriori that a significant percentage of conisations is not justified, whereas the operating part either proves healthy, or carrying light dysplasias with a strong probability of regressing spontaneously.

It is therefore desirable to have means enabling better differentiation of the gravity levels of the abnormalities detected as well as their extent so as to limit the number of conisations and/or to limit the size thereof. Moreover, in numerous countries colposcopy is performed as a first move, without any prior smears, which may lead to more numerous false positive results.

It is known that healthy and dysplastic tissues differentiate on the one hand by their architecture and on the other hand by the number and the size of their nucleus. These differences may hence modify the polarization of the back-scattered light and polarimetric imaging techniques may hence provide interesting results, complementary to those of conventional visual colposcopy, inasmuch as the eye is totally insensitive to polarization.

Generally, a polarimetric imaging system includes in its inlet arm a polarization state generator, so-called PSG, and in its output arm a polarization state analyser, so-called PSA. The purpose of the PSG is to define the polarization state sequence characterising the incident light on the sample and the PSA analyses the state of polarization of the light reflected by the sample, and this, for each of the incident polarization states defined by the PSG. According to the degree of characterisation desired in the polarimetric measurements, more or less complete modulation and analysis of polarization may be used.

We shall now remind briefly a few principles of polarimetric measurements applicable to imaging. For more detail it may be also referred to the patent application EP-1 411 333.

In the case of linear polarization degree imaging (linear DOP imaging), the PSG is a linear polariser arranged between a light source and the sample, and the PSA is an analyser, also a linear polariser, arranged between the sample and a camera. With such a device, two images are obtained, one with the parallel polariser and analyser ($I_{par}$) and the other with the perpendicular polariser and analyser ($I_{perp}$).

Typically, between both images the polariser will be rotated by 90° in its plane, wherein the analyser remains fixed to an azimuth angle (in its plane) α random. Alternately, it also possible to use a polarization separating device, for instance a polarising separating cube, and two cameras as indicated in J.R. Roman, K.Lee, S.A. Prahl, S.L. Jacques, <<Design, testing and clinical studies of a handheld polarized light camera >> Journal of Biomedical Optics 9, 1305 (2004). From the images obtained, the image is calculated in degree of polarization, so-called DOP »Degree Of Polarisation »defined by $$I_{DOP} = \frac{I_{par} - I_{perp}}{I_{par} + I_{perp}}$$

For random samples IDOP is theoretically ranging between −1 and +1. In practice, for samples of biological tissues, a priori depolarizing and isotropic ones, IDOP ranges between 0, for a totally depolarizing sample, and 1 when the incident polarization is kept totally.

In the case of circular polarization degree imaging (a variation of linear polarization degree imaging and wherein circular polarization means are implemented for PSG and PSA, the circular DOP is considered, defined by:

$$I_{DOP,circ} = \frac{I_{gg} - I_{gd}}{I_{gg} + I_{gd}}$$

where Igg and Igd designate respectively images acquired while illuminating the sample made of left-hand circular polarization and by detecting in left-hand or right-hand circular polarization.

In the case of Mueller imaging which enables to characterise completely any type of sample, and in particular highly depolarizing samples such as optically thick biological tissues, the PSG must provide a complete set of polarization states, that is to say at least four states whereof the Stokes vectors Si are linearly independent. These Stokes vectors are the column vectors of the modulation matrix W characterising the PSG. The reflection on the sample transforms each of these Stokes vectors Si in M Si, where M is the Mueller matrix of the sample. The PSA then determines these emerging Stokes vectors while projecting them against its four characteristic Stokes vectors, which must be linearly independent, as the basic states of the PSG, and which form the line vectors of the analysis matrix A characterising the PSA. At the end of the day, 16 raw images are obtained, which may be written (for each pixel) in the form of a product of real matrices 4×4

B=AMW

From these raw measurements is extracted the Mueller matrix M of the sample (which hence forms another set of 16 images) by reversal of the matrices A and W, after determination of these matrices by a known calibration procedure (one may also look up document EP-1 411 333 for instance) of the instrument. It appears that the most relevant criterion for optimising the design of a Mueller polarimeter consists in maximising the conditioning of the matrices A and W, i.e. the ratio of the smallest to the greatest of their single values. One may refer in this view to the articles of Compain, B. Drévillon, in Review of Scientific Instruments 69, 1574 (1998) or of J.S. Tyo, in Optics Letters 25, 1198 (2000). Regardless of the type of polarimeter, this ratio is limited to 0.577.

Mueller imaging is hence far more complicated to implement than DOP imaging, since it requires taking sixteenth images instead of two and the calibration of the instrument is also more difficult. Conversely, once the Mueller image acquired, it is very simple to derive using straightforward calculation all the images that could have been acquired in DOP linear imaging, for all azimuth angles α, or still DOP circular image. Moreover, contrary to the case of direct DOP imaging, it is thus possible to display for each pixel of the image the DOP at the angle α optimising for this pixel the required contrast, and this angle may be different from one pixel to the other, for instance because of an difference in incidence angle from one spot to the other of the analysed sample.

Finally, processes other than simple DOP calculation may be performed from of the Mueller matrix, such as for example polar decomposition of S. Lu and R. A. Chipman described in "Interpretation of Mueller matrices based on polar decomposition", J. Opt. Soc. Am. A. 13 (5), 1106, 1996, and may enable better restitution of the contrasts associated with the nature of the tissue properly speaking rather than with the conditions of observation. Mueller imaging hence enables an optimisation of the contrast unlike DOP imaging.

The invention offers therefore means enabling to implement colposcopy polarimetric imaging. These means may be coupled easily to a pre-existing colposcopy device in particular to reduce the cost of implementation, while also enabling conventional usage of said device. To this end a portion means may be inserted easily and retracted both physically (for the physical means) and functionally (for the functional means, in particular calculations, displays . . . ), so as to enable the physician to examine each female patient either in traditional colposcopy (in particular in high resolution binocular image or on a screen), or in polarimetric colposcopy. Moreover, the invention is applicable to various degrees of polarimetric characterisation of the cervix observed. It is thus that in its easiest version to implement but also the least complete as regards characterisation, it is possible to perform measurements with imaging only in linear or circular polarization degree. In a version more complex to implement, but which enables to characterise completely the polarimetric behaviour of the elements of the cervix, measurements will be taken using Mueller imaging. In the latter case, it should be understood that according to the motto "he who can do more can do less", taking into account the possible complete characterisation, one may at the end of the day consider only a portion of the results to limit oneself to linear or circular polarization degrees or other partial results.

Thus, the invention relates to an electronic polarimetric imaging system for a colposcopy device designed for in vivo observation of a cervix, wherein the colposcopy device comprises a light source for illuminating the observable cervix and at least visual means for monitoring an image of said cervix, the illumination optical path towards the cervix and the image optical path coming back from the cervix being separated from one another over at least one portion of the paths thereof.

According to the invention, the system comprises a polarimetric adapter housing which is removable into the separated portion of the illumination and image optical paths, said polarimetric adapter housing including a polarization state generator (PSG) on the illumination optical path and a polarization analyser (PSA) on the image optical path, wherein the polarization state generator (PSG) and the polarization analyser (PSA) are controllable.

It should be understood that the colposcopy device which includes at least visual observation means at least provides the user with visual direct observation. in case when only visual observation means are available, it will be preferable to adapt to said device an image electronic sensor and in case when said device already has an image sensor (in particular a camera) one may, possibly, use said sensor for imaging. it should be also understood that means for acquiring images from the sensor, for calculating/processing images and viewing results in the form of computer equipment are also implemented Similarly, the computer equipment enables electronic control of the different elements which may be controlled electronically from the system and in particular those of the adaptor housing. The computer equipment may also, in certain versions, need to act on the image sensor and/or any member associated therewith (a removable optical filter for instance) Finally, if the system is to in vivo measurements, it should be understood that it may also be applicable for ex vivo measurements, for instance on operating parts.

Within the framework of the invention, the term housing relates more generally to any means for supporting or holding PSGs and PSAs in their functional relationships together and with the colposcopy device in active/functional position. Thus the term housing may relate to a simple supporting plate whereon the members are arranged, as well as a closed box (obviously with material and functional openings for the passage of the optical paths) wherein the members are situated. The implementation of a box exhibits the advantage of being able to protect from the environment certain portions of the elements implemented in the adaptor housing.

In various embodiments of the invention, the following means which may be used single or according to all technically possible combinations, are used:

- the polarization state generator (PSG) and the polarization analyser (PSA) are controlled electronically, (mechano-electronically in case when an electrical motor is implemented)
- the polarization state generator (PSG) and the polarization analyser (PSA) are controlled mechanically, (the command may be manual)
- the colposcopy device comprising a front face in relation with the cervix with at least one illumination output pupil and at least one image input pupil, the removable polarimetric adapter housing is arranged in functional position on said front face of the device,
- the polarimetric adapter housing is removable by linear translation along said front face of the device,
- the polarimetric adapter housing is removable by tilting-over with rotation around an axis parallel to said front face of the device,
- the polarimetric adapter housing is removable by tilting-over with rotation around an axis perpendicular to said front face of the device,
- the colposcopy device comprising a first interchangeable portion in relation with the cervix and a second portion comprising the light source and the at least visual observation means, the removable polarimetric adapter housing is arranged between the first portion and the second portion of the device, wherein the first portion may be indifferently attached to the polarimetric adapter housing or to the second portion,
- the device includes moreover an image electronic sensor,
- the adapter housing includes moreover an image electronic sensor on the image optical path, (the image being intercepted by the sensor, in the case of a monocular device the visual means of the device cannot be used by the operator in the case of a binocular device, single one of the oculars remains useable by the operator, in all cases the user may refer to a visualisation monitor whereon the image from the sensor is displayed directly or after calculations), at least one optical filter is arranged upstream of the image electronic sensor, the optical filter has no effect on the visual observation, the optical filter is removable manually, the optical filter is removable by an electronic control, the optical filter in active position is selected among a set of selectable filters, the optical filter is a pass-band, the pass-band is centered approximately on one of the following wavelengths: 450 nm, 550 nm, 650 nm, the light source for illumination is wide-band, the light source for illumination is polychromatic, the light source for illumination is monochromatic, the light source for illumination is monochromatic of selectable wave-length, the light source for illumination is monochromatic of selectable wave-length with an emission peak centered approximately on one of the following wavelengths: 450 nm, 550 nm, 650 nm, the adapter housing includes moreover downstream of the polarization analyser (PSA) a semi-reflecting blade tilted on the image optical path and an image electronic sensor, wherein the semi-reflecting blade enables to sample a portion of the light signal on the image optical path to send it back to the sensor, (let alone that the image is effectively sent into the visual observation means, the image is also sent to the sensor and the user may hence use the visual observation means regardless whether the apparatus is monocular or binocular)

the observation means are monocular with a single image optical path, the observation means are binocular with two image optical paths and the polarization analyser (PSA) is arranged on one of both image optical paths, the observation means are binocular with two image optical paths and the polarization analyser (PSA) is arranged on the image optical path intended for the image electronic sensor, in case when the system may enable an ellipsometry (polarimetric measurements) complete according to the Mueller principles, the polarization state generator (PSG) or the polarization analyser (PSA) is a device selected among:

a device including a linear polarizer and two electronically controlled nematic liquid crystal modulators whereof the reference axes are situated at determined azimuths $\theta_{n1}$ and $\theta_{n2}$ respectively relative to the conducting axis of the linear polariser, a device including a linear polariser and two electronically controlled ferroelectric liquid crystal modulators whereof the reference axes are situated at determined azimuths $\theta_{f1}$ and $\theta_{f2}$ respectively relative to the conducting axis of the linear polariser, a device including a linear polariser and two electronically controlled ferroelectric liquid crystal modulators whereof the reference axes are situated at determined azimuths $\theta'_{f1}$ and $\theta'_{f2}$ respectively relative to the conducting axis of the linear polariser, wherein a fixed delay blade of determined orientation $\theta'_Q$ is interposed between both modulators, (the polarization state generator (PSG) or the polarization analyser (PSA) may be of the same type or of different types)

the system includes means such as:

in the case of a device including a linear polariser and two nematic liquid crystal modulators, the azimuths have as approximate values $\theta_{n1}=\epsilon 27.4°+q90°+/-10°$ and $\theta_{n2}=\epsilon 72.4°+90r°+/-10°$ with $\epsilon=+/-1$ and $q, r \in \mathbb{N}$, (q and r are integers not necessarily equal)

in the case of a device including a linear polariser and two ferroelectric liquid crystal modulators, the azimuths have as approximate values $\theta_{f1}=70°+/-5°$ and $\theta_{f2}=165°+/-5°$, in the case of a device including a linear polariser, two ferroelectric liquid crystal modulators and a fixed delay blade, the azimuths have as approximate values $\theta'_{f1}=-10°+/-5°$ and $\theta'_{f2}=71°+/-5°$ and $\theta'_Q=-5°+/-2°$, in case when the system may enable only linear DOP imaging, the polarization state generator (PSG) is a linear polariser and the polarization analyser (PSA) includes an electronically controlled ferroelectric liquid crystal modulator and a linear polariser provided with an electronically controlled polarization angle, in case when the system may enable only linear DOP imaging with azimuth adjustment α, the polarization state generator (PSG) is a linear polariser and the polarization analyser (PSA) includes an electronically controlled ferroelectric liquid crystal modulator, a linear polariser and a quarter wave blade interconnected with said linear polariser, wherein the quarter wave blade interconnected with said linear polariser has a reference axis of 45° relative to that of the linear polariser, and the polarization state generator (PSG) and the polarization analyser (PSA) are mounted rotatably and controlled electronically synchronously and rotatably by an angle α, (so as to maintain the same relation of the reference axes of the elements forming the polarization state generator (PSG) and the polarization analyser (PSA) therebetween and during the rotation by an angle α)

the quarter wave blade interconnected with said linear polariser of the polarization analyser (PSA) is a blade made of mica or a plastic sheet, in particular of the type of those offered by American Polarizers Inc. (API) and manufactured by 3M, the dichroic polariser is also a plastic sheet of the type of those offered by American Polarizers Inc. (API) under the references HNxx, the linear polariser and the quarter wave blade are directly assembled into a circular polariser, (by way of example: the HNCP polarizers of API, or still the numerous circular polarizers offered by the manufacturers of photo accessories, providing the extinction of the linear polariser integrated to these filters is verified, wherein the residual transmission should be typically of the order of the per-cent at the working wavelength)

the electronic control includes a motor whereof the rotor meshes on the one hand into a first toothed ring containing internally the polarization state generator (PSG) and on the other hand a second toothed ring containing internally the polarization analyser (PSA), in case when the system may enable only a circular ellipsometry, the polarization state generator (PSG) is a circular polariser and the polarization analyser (PSA) includes an electronically controlled ferroelectric liquid crystal modulator, a linear polariser and a quarter wave blade interconnected with said linear polariser.

The invention also relates to an adaptor housing for a colposcopy device designed for in vivo observation of a cervix enabling to provide an electronic polarimetric imaging system, wherein the colposcopy device comprises a light source for illuminating the observable cervix and at least visual means for monitoring an image of said cervix, the illumination optical path towards the cervix and the image optical path coming back from the cervix being separated from one another over at least one portion of the paths thereof, in which invention, the polarimetric adapter housing is removable and intended for being arranged in the separated portion of the illumination and image optical paths, said polarimetric adapter housing including a polarization state generator (PSG) on the illumination optical path and a polarization analyser (PSA) on the image optical path, the polarization state generator (PSG) and the polarization analyser (PSA) being controlled.

Moreover, the adapter housing of the invention may also include one or several of the features listed previously pertaining thereto.

The invention thus enables the acquisition of the images in parallel and crosses polarizations in automated fashion under electronic control, without the physician needing to intervene directly on the optical means implemented. The electronic control also enables to benefit from a high acquisition speed of the images in parallel and crossed polarizations which limit the risks of artifacts due to the possible movements of the female patient between two acquisitions. Similarly, in the case of a direct acquisition system of linear DOP imaging, the azimuth α of the common polarization of the incident light as detected in $I_{par}$ may be adjusted easily for optimising the contrast contrary to the conventional devices. Finally, the arrangement of the means implemented enables to avoid the artifacts associated with the internal optics of the colposcopy device, in particular due to separators.

Figure 2:
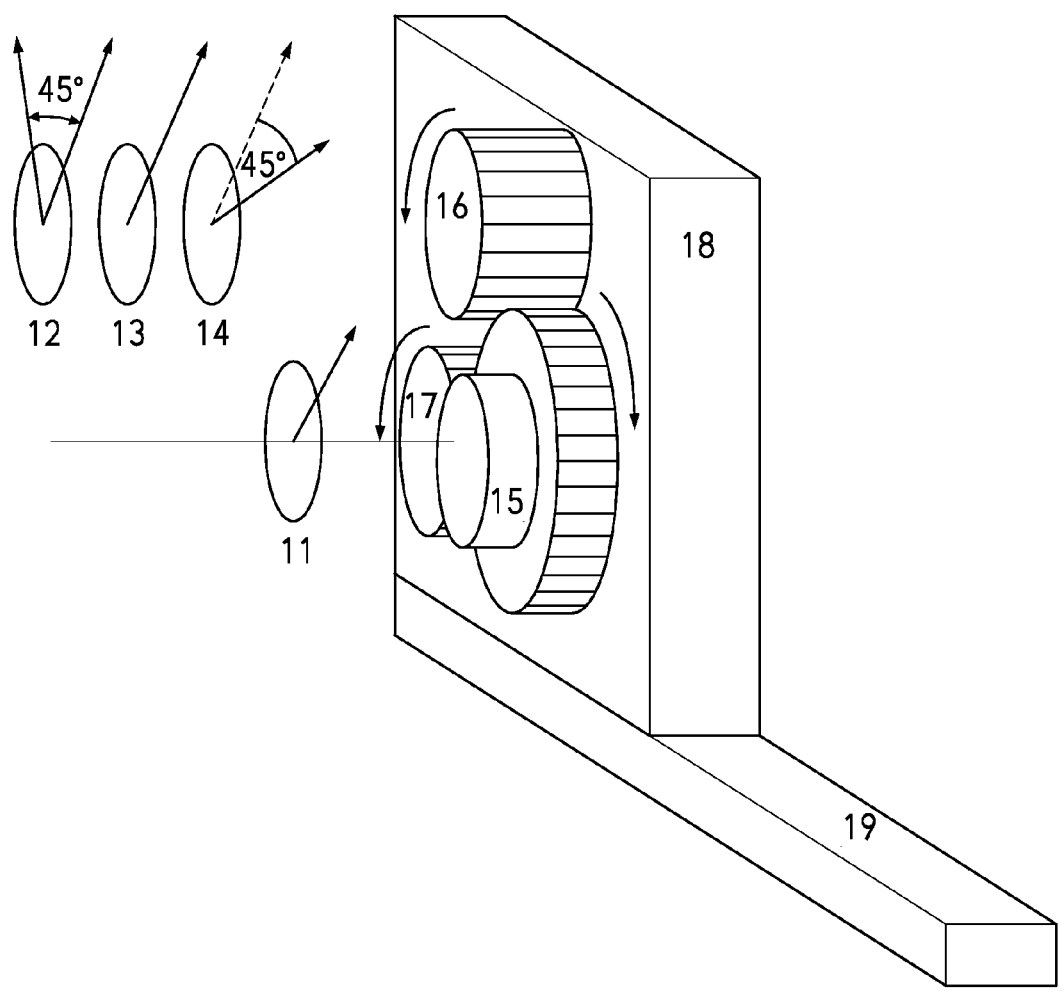
Figure 3:
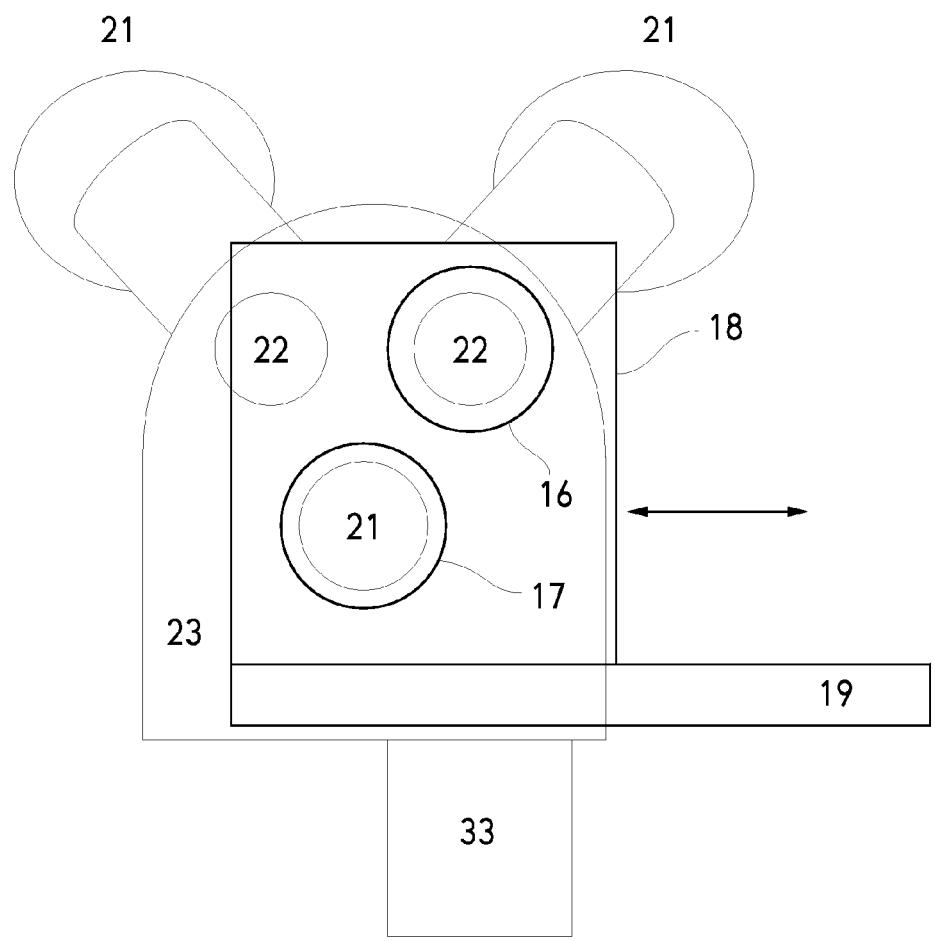
Figure 4:
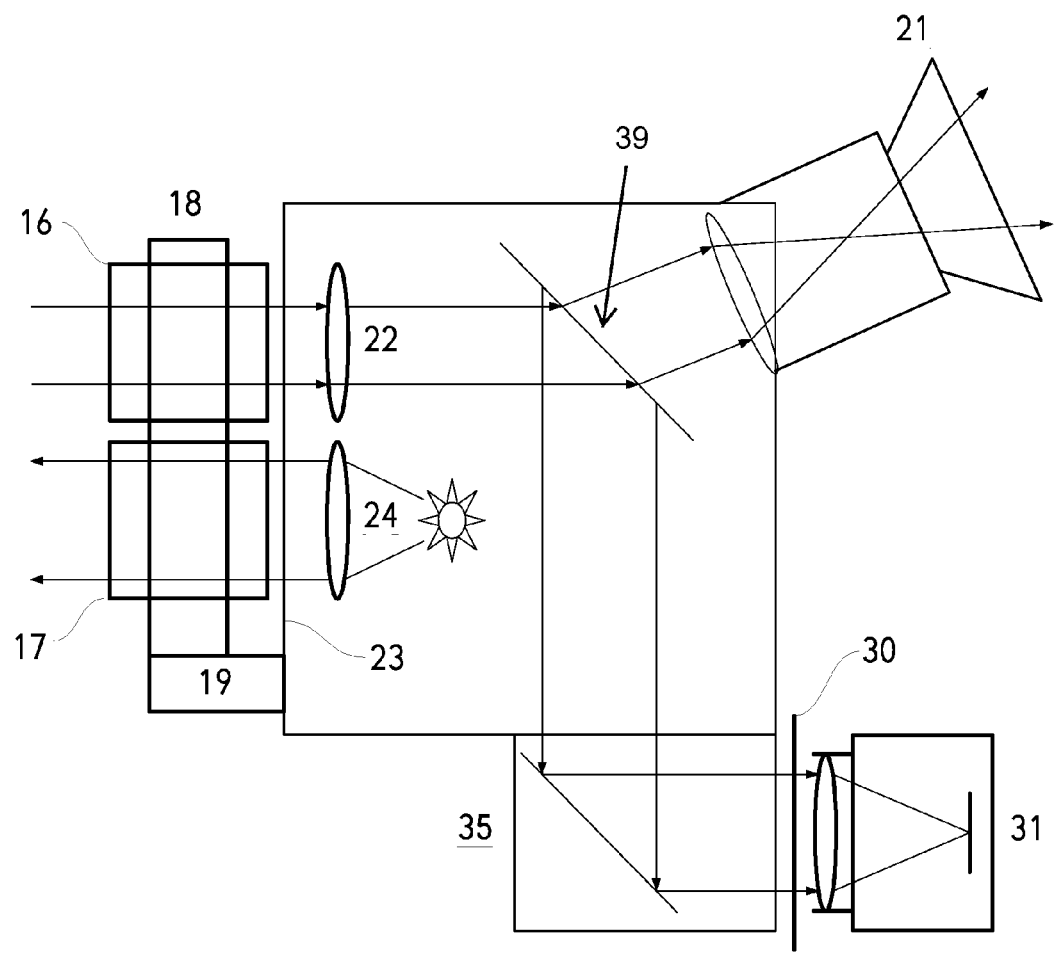
Figure 5:
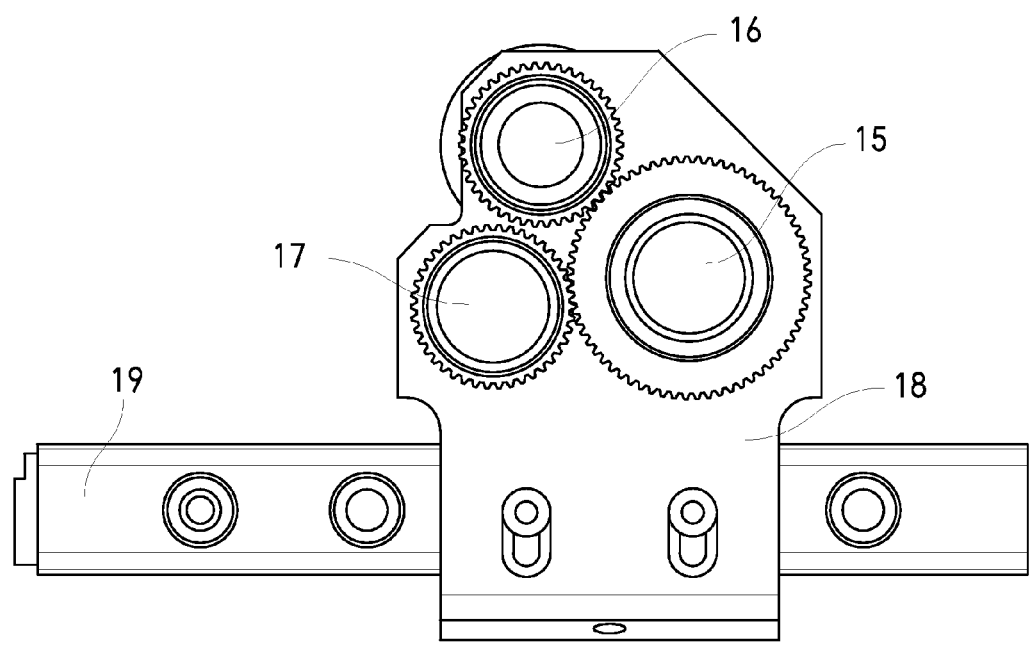
Figure 6:
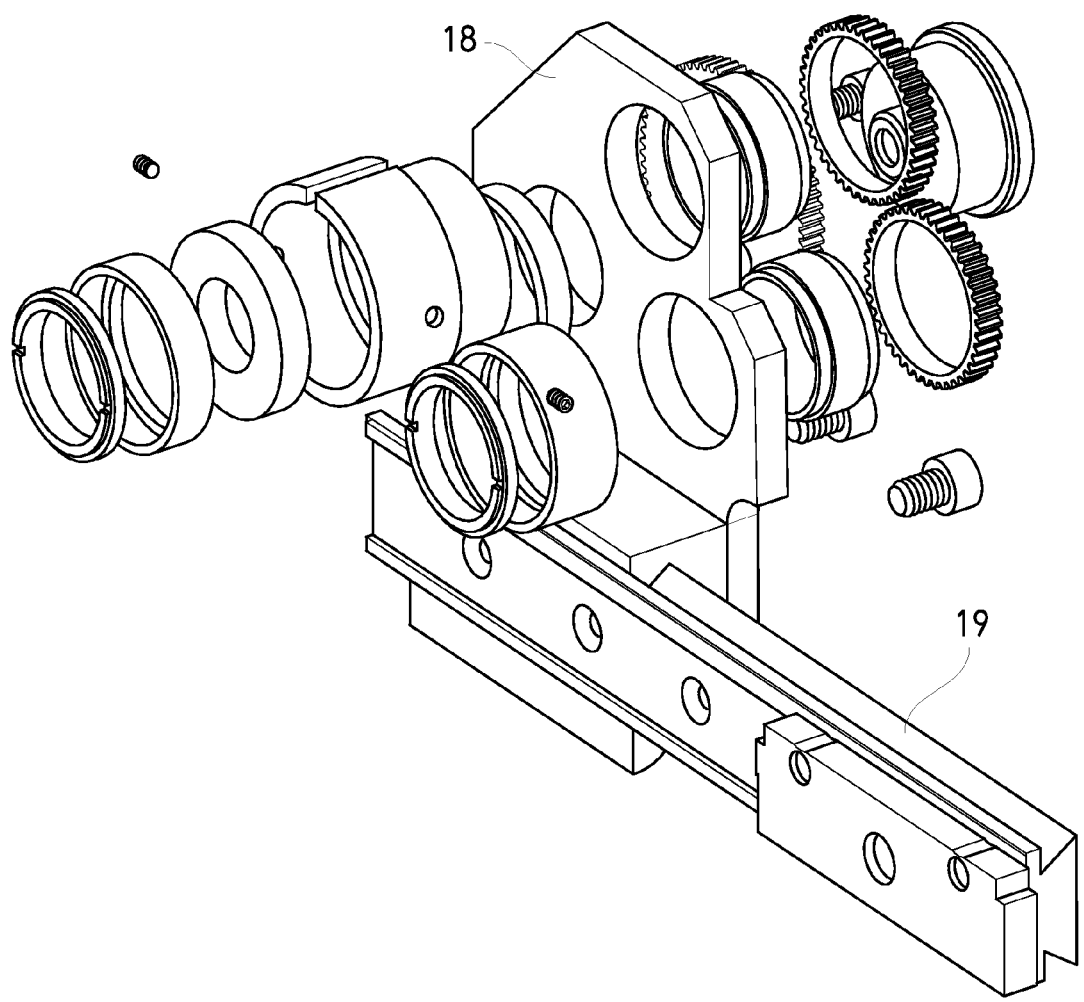

The present invention will now be exemplified without being limited thereto with the following description in relation with the Figures below:

FIG. 1 which represents diagrammatically the structure of a PSG or of a PSA provided with liquid crystals for Mueller imaging, FIG. 2 which represents diagrammatically in perspective an adaptor housing for linear imaging with adjustable azimuth, FIG. 3 which represents diagrammatically a front view of an adaptor housing on the front face of a typical colposcopy device, FIG. 4 which represents diagrammatically a front view of an adaptor housing on the front face of a typical colposcopy device, FIG. 5 which represents a front view of an embodiment of an adaptor housing for linear imaging with adjustable azimuth of the type of that of FIG. 2, and FIG. 6 which represents a perspective exploded view of the adaptor housing for linear imaging with adjustable azimuth of the type of FIG. 5.

The system of the invention enables to use a colposcopy device for conducting polarimetric characterizations of cervices while leaving the possibility to the user of employing his colposcopy device conventionally. To do so a removable adaptor housing is implemented as well as imaging means fitted with an image sensor (in an enhanced mode). The image sensor may be available in the colposcopy device and, preferably, it will be used or, failing which, one will be installed in the colposcopy device. In the latter case, the manufacturer may have provided such an image sensor installation in option or, failing which, the image sensor may be arranged removable in relation with a/the ocular of the colposcopy device.

Thus, polarimetric imaging means are combined with a colposcopy device. The modulation (PSG) and the analysis (PSA) of the polarization are performed by optical systems using polarizers and liquid crystals situated at the front of the colposcopy device. These liquid crystals are controlled by computer equipment also managing the acquisition by an image sensor, a CCD camera in this case and situated at the rear of the colposcopy device and, preferably, fitted with a filter selecting the most appropriate wavelength which is typically in the green. The liquid crystals PSG and PSA implemented enable to modulate and analyse the polarization rapidly and are compact since the space requirements of the PSG and PSA are very small, transversally as well as longitudinally.

We shall now describe the PSG and PSA useable in the adaptor housing for Mueller imaging. Generally speaking, the PSG and PSA include a linear polariser, which, for the application contemplated, is placed against the front face of the colposcopy device, and two liquid crystal modulators whereof the reference axes are situated at azimuths $\theta_1$ and $\theta_2$ relative to the conducting axis of the linear polariser as represented on FIG. 1. Thus in a PSG or a PSA, on an optical path 1-2, 1 being towards the front face of the colposcopy device and 2 being towards the observable cervix, there is a linear polariser 3 with a direction 6 of the conducting axis of the linear polariser and two electronically controlled liquid crystal modulators 4 and 5 and which follow the reference axes 7, 8 of the liquid crystals in the plane of the modulators. This type of PSG and PSA enables to obtain any polarimetric information without needed to move any optical element (except for the adapter housing as a whole to retract it) and hence the PSG and PSA might be fastened, in this case to a support 18 (FIG. 2 or 3) without any possibility of individual rotation.

For optimal performances, the concrete orientation of the PSG and PSA is typically imposed by the dichroism of the colposcopy device. For instance, during tests, it has been observed that the intensity transmitted to the CCD camera was much smaller, by more than a 10-factor, in vertical polarization than in horizontal polarization, which can be explained by the presence of standard separators in the colposcopy device which was used for testing. We might then be led to adjust the orientations of the PSG and PSA relative to the colposcopy device used in the system of the invention. This adjustment, performed once and for all, is however not critical.

On the other hand, it may prove useful to perform a calibration procedure which is known in itself (for instance into the patent application EP-1,411,333) to define the origin of the azimuth angles independently of the actual orientation of the PSG and PSA in the adaptor housing: this origin only depends in fact on the orientation of the additional optical elements (polarizers, delay blades) used during the calibration procedure.

We have hence described schematically the PSG and PSA useable for Mueller imaging. Concretely, several embodiments of the PSG and PSA are useable. Thus, in addition to linear polarizers, the PSG and PSA may include either two nematic liquid crystals, or two ferroelectric liquid crystals, or two ferroelectric liquid crystals and one fixed delay blade between both.

In the case of two nematic liquid crystals, there is an equivalence with delay blades of fixed orientation and variable delay, controlled electronically. For this type of modulator, the reference axis in the plane corresponds to the extraordinary axis, of variable index. The polarization states Si are generated in sequence, while imposing delays ($\delta_1, \delta_2$) to both liquid crystals in a sequence in the form therebelow $$(\delta_1,\delta_2)=(\Delta_1,\Delta_1),(\Delta_2,\Delta_1),(\Delta_1,\Delta_2),(\Delta_2,\Delta_2),$$

This configuration enables to hold the conditioning of the matrices A and W close to the optimal value 0.577 regardless of the wavelength (at least in the visible and the near-infrared) for the following values of the parameters:

$$\theta_1=\epsilon 27.4°+q90° \text{ and } \theta_2=\epsilon 72.4°+r90°,$$

$$\Delta_1=315°+p90° \text{ and } \Delta_2 135°+p90°,$$

with $\theta_1$ and $\theta_2$ within +/−10° and where $\epsilon=\pm 1$ has the same value in both equations, whereas q and r are any integers (not necessarily equal).

In the case of two ferroelectric liquid crystals there is an equivalence with delay blades whereof the delay is fixed and that the electronic control toggles between two 45° orientations relative to one another, without changing the value of the delay. The four Stokes vectors Si of the PSG and of the PSA are hence obtained, starting from an initial state (for the PSG) or final state (for the PSA) polarised linearly by traversing both ferroelectric blades whereof the orientations of the slow axes take successively the values:

$$(\theta_1,\theta_2),(\theta_1+45°,\theta_2),(\theta_1,\theta_2+45°),(\theta_1+45°,\theta_2+45°)$$

With respect to the pneumatics, the ferroelectrics exhibit the advantage of toggling far more quickly, but they do not enable to hold an optimal conditioning over as wide a spectral range. Nevertheless, with commercial modulators, specified as 510-nm semi-wave and quarter-wave, acceptable conditioning is obtained (greater than 0.4) over the whole spectral range between 500 and 650 nm, for the following orientations:

$$\theta_1=70°\pm 5°,\theta_2=165°\pm 5°$$

In the case of two ferroelectric liquid crystals and one fixed delay blade between both. The same ferroelectrics may be used in substantially wider a spectral range (from 450 to 750 nm) if a fixed delay blade is interspaced therebetween, in quartz, specified as 633-nm quarter-wave. The orientations of these three elements are then as follows:

$$\theta_1=-10°\pm 5°,\theta_Q=-5°\pm 2°\theta_2 71°\pm 5°$$

We shall now describe the system in the limited case of linear DOP characterisation. In order to implement linear DOP imaging with adjustable azimuth, the PSG may be reduced to a linear polariser and the PSA to a ferroelectric and a linear analyser. The conducting axes of the linear polariser and of the linear analyser being parallel, it suffices to switch the ferroelectric in order to acquire in sequence, and within a very short time, the images in parallel and crosses polarizations. The corresponding system is illustrated on FIGS. 2 to 6 and enables to acquire linear DOP images, while adjusting easily the azimuth α of the incident polarization without misaligning the linear polariser and analyser. To this end, the PSG and PSA are inserted into toothed rings driven by the same control toothed wheel. Moreover, to avoid too great variations in the intensity detected with the azimuth, a quarter wave blade is placed behind the linear analyser, interconnected with said analyser and whereof the axes are tilted at 45° in relation thereto, to convert the linear polarization after the analyser in circular polarization, theoretically independent from the azimuth α: the intensity finally detected must hence be independent from α, even for a colposcopy device exhibiting large linear dichroism. The linear polariser quarter-wave blade assembly may be advantageously replaced with a circular polariser associating both these elements in a plastic sheet whose aspect is analogue to the conventional dichroic polarizers of »Polaroid® »type, providing however that the extinction rate of the linear polariser included in this circular polariser is sufficient (of the order of 100 or more). It should be noted that alternately, nothing prevents from placing the ferroelectric in the PSG, after the linear polariser, and to reduce the PSA to the single circular polariser.

FIG. 2 enables to visualize the adapter housing which is in this embodiment a simple support 18 mounted slidingly on a rail 19 so as to enable the retraction thereof from the front face of a colposcopy device when the latter must be used conventionally. The PSG 17 is fixed in a toothed ring and the left-hand portion of the figure represents its function in the form of a linear polariser 11 with the arrow indicating the direction of the conducting axis. The PSA 16 is fixed in a toothed ring and the left-hand portion of the figure represents its function in the form of the combination of a ferroelectric liquid crystal 12 (the arrows point out to both possible directions of the slow axis), of a linear analyser 13 whereof the conducting axis (arrow) is parallel to that of the polariser 11 of the PSG and of a quarter wave blade 14 at 45° of the axis of the polariser and analyser. A toothed wheel 15 meshes into the rings carrying the PSG and PSA. The toothed wheel may be controlled manually so as to locate the best angle α of azimuth and/or, in a variation, controlled electronically (motorized system). The front face of the colposcopy device (not represented on FIG. 2) is on the right of Figure and the observation direction of the cervix on the left.

FIGS. 3 and 4 enable to visualize the functional and structural relations between the adaptor housing and the colposcopy device in the system of the invention. On these figures, the adapter housing, comprising a supporting plate 18 in that case, is represented as a thick line whereas the colposcopy device is represented as a thin line. The image sensor has also been represented as a thick line but it should be reminded that it may also be part of the colposcopy device (accessory supplied) or that it may be added to suit the requirements of DOP imaging.

The colposcopy device is here of the binocular type with two oculars or eyepiece diaphragms 21 backwards for visual observation. On the front face 23 of the colposcopy device there are two inlet pupils 22 of the binocular imaging system and an outlet pupil 24 of the illumination system. The colposcopy device includes an outlet for taking images whereon there are an optical filter 30 and a CCD camera 31. Images are taken on one of both images of the binocular system thanks to a blade 39 represented as a discontinuous line on FIG. 4. The front face of the colposcopy device in the removable adaptor housing includes the polarization state analyser (PSA) 16 and the polarization state generator (PSG) 17 which are on a supporting plate 18 common to the PSG and PSA and which may slide (as specified by the arrow in thick line on FIG. 3) on the rail 19 and enabling thus the retraction thereof.

FIG. 5 is a concrete embodiment of the adaptor housing of the type represented schematically on FIGS. 3 and 4 as a front view and FIG. 6 a exploded perspective view.

In a variation, it is possible to perform circular DOP imaging which exhibits the advantage of suppressing the requirement of rotating the PSG and PSA for optimising the contrast, but the latter will be a priori weaker than in linear DOP for an optimised orientation of the azimuth angle α. To implement this variation, it suffices that the PSG is formed of a circular polariser and the PSA of a circular analyser alternately left and right, obtained by placing a semi-wave ferroelectric crystal between the linear polariser and the quarter wave blade forming the circular analyser. Alternately, these three elements can also be located in the PSG to limit the PSA to a circular analyser.

Experiments have been conducted in linear DOP imaging on operating parts ex vivo (just after exercise) of cervices, after shipment to the anatomopathologist. The contrasts visible on the images have been compared with the indications of the anatomopathology report. Several wavelengths have been used DOP imaging could put in evidence severe dysplasias which were invisible on non-polarised images. One could notice on the images that the contrast varied highly in relation to the azimuth angle α defining the common orientation of the polariser and analyser for the image acquisition ($I_{par}$). This dependency is probably associated with the high incidence under which the tissue of the cervix is observed in the central zone of the organ (inlet to the endocervix). Circular DOP imaging enables a prior to break free from any dependency to the contrast relative to the azimuth α which is observed in linear DOP but at the cost of a contrast slightly smaller than in azimuth optimised linear DOP.

The invention claimed is:

1. An electronic polarimetric imaging system for use with a colposcopy device designed for in vivo observation of a cervix, wherein the colposcopy device comprises a light source for illuminating the observable cervix and at least visual means for monitoring an image of said cervix, an illumination optical path towards the cervix and an image optical path coming back from the cervix being separated from one another over at least one portion of paths thereof, said electronic polarimetric imaging system comprising:

a polarimetric adapter housing which is removable into
i) a first separated optical path of the illumination optical path towards the cervix, the first optical path separated from the image optical path coming back from the cervix, and
ii) a second separated optical path of the image optical path coming back from the cervix, the second optical path separated from the illumination optical path towards the cervix,
said polarimetric adapter housing including
i) a polarisation state generator (PSG) on the first separated optical path of the illumination optical path, and
ii) a polarisation analyser (PSA) on the second separated optical path of the image optical path,
wherein at least one of the polarization state generator (PSG) and the polarization analyser (PSA) comprises a linear polariser and an electronically controlled liquid crystal modulator whereof reference axes are situated at determined azimuths relative to the conducting axis of the linear polariser, and
wherein the polarisation state generator (PSG) and the polarisation analyser (PSA) are each controllable,
the polarimetric adapter housing being removable from the colposcopy device to leave the colposcopy device functional for in vivo observation of the cervix in a non-polarimetric mode.

2. A system according to claim 1, wherein, with the colposcopy device comprising a front face in relation with the cervix with at least one illumination output pupil and at least one image input pupil,
said electronic polarimetric imaging system further comprises the removable polarimetric adapter housing arranged in functional position on said front face of the colposcopy device.

3. A system according to claim 2, wherein, the polarimetric adapter housing is removable by at least one of a linear translation along said front face of the colposcopy device,
a tilting-over with rotation around an axis parallel to said front face of the colposcopy device, and
a rotation around an axis perpendicular to said front face of the colposcopy device.

4. A system according to claim 2, wherein, the colposcopy device further includes an image electronic sensor.

5. A system according to claim 2, wherein, the adapter housing further includes an image electronic sensor on the second separated optical path of the image optical path.

6. A system according to claim 2, wherein,
the adapter housing further includes, downstream of the polarisation analyser (PSA), i) a semi-reflecting blade tilted on the image optical path and ii) an image electronic sensor,
the semi-reflecting blade sampling a portion of a light signal on the image optical path and sending the sampled portion of the light signal back to the electronic sensor.

7. A system according to claim 2, wherein, with the system completely enabling ellipsometry according to the Mueller principles, the polarization state generator (PSG) and the polarization analyzer (PSA) is one of:
a device including a linear polarizer and two electronically controlled nematic liquid crystal modulators whereof reference axes are situated at determined azimuths $θ_{n1}$ and $θ_{n2}$ respectively relative to the conducting axis of the linear polarizer,
a device including a linear polarizer and two electronically controlled ferroelectric liquid crystal modulators whereof reference axes are situated at determined azimuths $θ_{f1}$ and $θ_{f2}$ respectively relative to the conducting axis of the linear polarizer, and
a device including a linear polarizer and two electronically controlled ferroelectric liquid crystal modulators whereof reference axes are situated at determined azimuths $θ'_{f1}$ and $θ'_{f2}$ respectively relative to the conducting axis of the linear polarizer, wherein a fixed delay blade of determined orientation $θ'_Q$ is interposed between both modulators.

8. A system according to claim 2, wherein,
the system enables only linear DOP imaging, and
the polarisation state generator (PSG) is a linear polariser and the polarisation analyser (PSA) includes an electronically controlled ferroelectric liquid crystal modulator and a linear polariser provided with an electronically controlled polarisation angle.

9. A system according to claim 2, wherein,
the system enables only linear DOP imaging with azimuth setting α,
the polarisation state generator (PSG) is a linear polariser and the polarisation analyser (PSA) includes an electronically controlled ferroelectric liquid crystal modulator, a linear polariser and a quarter wave blade interconnected with said linear polariser, and
the quarter wave blade interconnected with said linear polariser has a reference axis of 45° relative to that of the linear polariser, and in that the polarisation state generator (PSG) and the polarisation analyser (PSA) are mounted rotatably and controlled electronically synchronously and rotatably by an angle α.

10. A system according to claim 2, wherein,
the system enables only circular ellipsometry, and
the polarisation state generator (PSG) is a circular polariser and the polarisation analyser (PSA) includes an electronically controlled ferroelectric liquid crystal modulator, a linear polariser and a quarter-wave blade interconnected with said linear polariser.

11. A system according to claim 1, wherein the colposcopy device further includes an image electronic sensor.

12. A system according to claim 1, wherein the adapter housing further includes an image electronic sensor on the second separated optical path of the image optical path.

13. A system according to claim 1, wherein,
the adapter housing further includes, downstream of the polarisation analyser (PSA), i) a semi-reflecting blade tilted on the image optical path and ii) an image electronic sensor,
the semi-reflecting blade sampling a portion of a light signal on the image optical path and sending the sampled portion of the light signal back to the electronic sensor.

14. A system according to claim 1, wherein, with the system completely enabling ellipsometry according to the Mueller principles, the polarization state generator (PSG) and the polarization analyzer (PSA) is one of:
a device including a linear polarizer and two electronically controlled nematic liquid crystal modulators whereof reference axes are situated at determined azimuths $\theta_{n1}$ and $\theta_{n2}$ respectively relative to the conducting axis of the linear polarizer,
a device including a linear polarizer and two electronically controlled ferroelectric liquid crystal modulators whereof reference axes are situated at determined azimuths $\theta_{f1}$ and $\theta_{f2}$ respectively relative to the conducting axis of the linear polarizer, and
a device including a linear polarizer and two electronically controlled ferroelectric liquid crystal modulators whereof reference axes are situated at determined azimuths $\theta'_{f1}$ and $\theta'_{f2}$ respectively relative to the conducting axis of the linear polarizer, wherein a fixed delay blade of determined orientation $\theta'_Q$ is interposed between both modulators.

15. A system according to claim 14, wherein,
for the device including the linear polariser and the two nematic liquid crystal modulators, the azimuths have as approximate values $\theta_{n1}=\epsilon 27.4°+q90°+/-10°$ and $\theta_{n2}=\epsilon 72.4°+r90°+/-10°$ with $\epsilon=+/-1$ and $q, r \in N$,
for the device including the linear polariser and the two ferroelectric liquid crystal modulators, the azimuths have as approximate values $\theta_{f1}=70°+/-5°$ and $\theta_{f2}=165°+/-5°$,
for the device including the linear polariser, the two ferroelectric liquid crystal modulators and the fixed delay blade, the azimuths have as approximate values $\theta'_{f1}=-10°+/-5°$ and $\theta'_{f2}=71°+/-5°$ and $\theta'_Q=-5°+/-2°$.

16. A system according to claim 1, wherein,
the system enables only linear DOP imaging, and
the polarisation state generator (PSG) is a linear polariser and the polarisation analyser (PSA) includes an electronically controlled ferroelectric liquid crystal modulator and a linear polariser provided with an electronically controlled polarisation angle.

17. A system according to claim 1, wherein,
the system enables only linear DOP imaging with azimuth setting $\alpha$,
the polarisation state generator (PSG) is a linear polariser and the polarisation analyser (PSA) includes an electronically controlled ferroelectric liquid crystal modulator, a linear polariser and a quarter wave blade interconnected with said linear polariser, and
the quarter wave blade interconnected with said linear polariser has a reference axis of 45° relative to that of the linear polariser, and in that the polarisation state generator (PSG) and the polarisation analyser (PSA) are mounted rotatably and controlled electronically synchronously and rotatably by an angle $\alpha$.

18. system according to claim 17, wherein,
the synchronous electronic control includes a motor, and
rotor meshes i) into a first toothed ring containing internally the polarisation state generator (PSG) and ii) a second toothed ring containing internally the polarisation analyser (PSA).

19. system according to claim 1, wherein,
the system enables only circular ellipsometry, and
the polarisation state generator (PSG) is a circular polariser and the polarisation analyser (PSA) includes an electronically controlled ferroelectric liquid crystal modulator, a linear polariser and a quarter-wave blade interconnected with said linear polariser.

20. A polarimetric adaptor housing for use with a colposcopy device designed for in vivo observation of a cervix enabling to provide an electronic polarimetric imaging system, wherein the colposcopy device comprises a light source for illuminating the observable cervix and at least visual means for monitoring an image of said cervix, an illumination optical path towards the cervix and an image optical path coming back from the cervix being separated from one another over at least one portion of paths thereof, said polarimetric adapter housing comprising:
a polarisation state generator (PSG) on a first separated optical path of the illumination optical path towards the cervix, the first separated optical path of the illumination optical path being separated from the image optical path coming back from the cervix; and
a polarisation analyser (PSA) on a second separated optical path of the image optical path coming back from the cervix, the second separated optical path of the image optical path being separated from the illumination optical path towards the cervix,
wherein at least one of the polarization state generator (PSG) and the polarization analyser (PSA) comprises a linear polariser and an electronically controlled liquid crystal modulator whereof reference axes are situated at determined azimuths relative to the conducting axis of the linear polariser,
wherein the polarisation state generator (PSG) and the polarisation analyser (PSA) are controllable, and
wherein the polarimetric adapter housing is removable and configured for arranging in the first separated optical path and the second separated optical path,
the polarimetric adapter housing being removable from the colposcopy device to leave the colposcopy device functional for in vivo observation of the cervix in a non-polarimetric mode.

* * * * *